(12) United States Patent
Bartlett

(10) Patent No.: US 6,288,098 B1
(45) Date of Patent: *Sep. 11, 2001

(54) PHARMACEUTICALS FOR THE TREATMENT OF REJECTION REACTIONS IN ORGAN TRANSPLANTATIONS

(75) Inventor: Robert Ryder Bartlett, Darmstadt (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/997,723

(22) Filed: Dec. 23, 1997

Related U.S. Application Data

(62) Division of application No. 07/932,577, filed on Aug. 20, 1992, now Pat. No. 5,728,721.

(30) Foreign Application Priority Data

Aug. 22, 1991 (DE) .................................. 41 27 737

(51) Int. Cl.[7] ............................ A61K 31/42; A61P 37/06

(52) U.S. Cl. .......................................... 514/378; 514/885

(58) Field of Search .................................. 514/378, 626, 514/885

(56) References Cited

U.S. PATENT DOCUMENTS

| 4,061,761 | 12/1977 | Ertel et al. . | |
| 4,087,535 | 5/1978 | Heubach | 514/378 |
| 4,284,786 | 8/1981 | Kammerer et al. | 548/248 |
| 4,351,841 | 9/1982 | Kammerer et al. | 424/272 |
| 4,636,513 | 1/1987 | Kammerer et al. | 514/326 |
| 4,965,276 | 10/1990 | Bartlett et al. | 514/378 |
| 5,100,899 | 3/1992 | Calne . | |
| 5,268,382 | 12/1993 | Bartlett et al. | 514/378 |
| 5,624,946 | 4/1997 | Williams | 514/378 |

FOREIGN PATENT DOCUMENTS

| 2076555 | 2/1993 | (CA) . |
| 2081173 | 4/1993 | (CA) . |
| 3534440A1 | 4/1987 | (DE) . |
| 4101324A1 | 7/1992 | (DE) . |
| 013 376 B1 | 7/1980 | (EP) . |
| 0 217 206 | 4/1987 | (EP) . |

OTHER PUBLICATIONS

*Auchincloss, Jr., "Xenogeneic Transplantations", Transplantation, 46(1):1–20.
*Ivan M. Roitt et al., "Immunology", ch. 24 "Transplantation and Rejection", pp. 24.1 to 24.9, Gower Medical Publishing (1985).
*K. Ulrichs et al., "Suppression of Natural Xenophile Antibodies with the Novel Immunomodulating Drug Leflunomide," Transplantation Proceedings, vol. 24, No. 2 (Apr. 1992), pp. 718–719.
*C.C.A. Kuchle et al., "Prevention of Kidney and Skin Graft Rejection Rates by Leflunomide a New Immunolodulating Agent," Transplantation Proceedings, vol. 23, No. 1 (Feb. 1991), pp. 1083–1086.
*D.B.J. Herrmann et al., "Drugs in Autoimmune Diseases," Klinische Wochenschrift, vol. 68 (Suppl. XXI)(1990), pp. 15–25.
*Bartlett et al., "Leflunomide (HWA 486), a novel immunomodulating compound for the treatment of autoimmune disorders and reactions leading to transplantation rejection," Agents Actions, vol. 32, Nos. 1/2, 32:10–21 (1991).
Bartlett et al., "Development of Autoimmunity in MRL/lpr Mice and the Effects of Drugs on this Murine Disease," Scand. J. Rheumatology, S75:290–299 (1988).
Bretzel et al., "Experimental Islet Transplantation in Small Animals," Pancreatic Islet Cell Transplantation, C. Ricardi, e., R.G. Landis Co., Austin, TX (1992).
Chong et al., "Leflunomide, a Novel Immunomodulatory Agent: In Vitro Analyses of the Mechanism of Immunosuppression," Transplantation Proceedings, 25:747–749 (1993).
Chong et al., "Leflunomide, a Novel Immunosuppressive Agent," Transplantation, 55;1361–1366 (1993).
Cosenza et al., "Combination Therapy with Brequinar Sodicum and Cyclosporine Synergistically Prolongs Hamster-to-Rat Cardiac Xenograft Survival," J. Heart Lung Transplantation, 13:489–497 (1994).
Fontana et al., "Long-Term Follow-Up of Human Islet Autotransplantation," Transplantation Proceedings, 26:581 (1994).
Foster et al., "Leflunomide Immunosuppression in Rat Small Intestinal Transplantation," Transplantation Proceedings, 26:1599–1600 (1994).
Glant et al., "Immunomodulation of proteoglycan–induced progressive polyarthritis by leflunomide," Immunopharmacology, 23:105–116 (1992).

(List continued on next page.)

Primary Examiner—Edward J. Webman
(74) Attorney, Agent, or Firm—Finnegan, Henderson, Farabow, Garrett & Dunner, L.L.P.

(57) ABSTRACT

The use compound 1 and/or 2 of the formulae

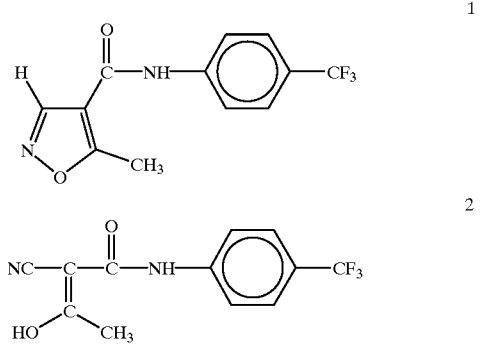

and of physiologically tolerable salts of compound 2 for the treatment of rejection reactions of the organ recipient to the transplanted organ is described.

9 Claims, No Drawings

OTHER PUBLICATIONS

Hayry et al., "Chronic Allograft Rejection," Imunological Reviews, 134:33–81 (1993).

Horak et al., "T–lymphocyte interleukin 2–dependent tyrosine protein kinase signal transduction involves the activation of p56$^{lck}$," Proc. Natl. Acad. Sci. USA, 88:1996–2000 (1991).

Kahan et al., "Synergistic Interactions of Cyclosporine and Rapamycin to Inhibit Immune Performances of Normal Human peripheral Blood Lymphocytes In Vitro," Transplantation, 51:232–239 (1991).

Küchle et al., "Prevention of Kidney and Skin Graft Rejection in Rats by Leflunomide, a New Immunomodulating Agent," Transplantation Proceedings, 23:1083–1086 (1991).

Mattar et al., "Inhibition of the epidermal growth factor receptor tyrosine kinase activity by leflunomide," FEBS Letters, 334:161–164 (1993).

McChesney et al., "An Evaluation of Leflunomide in the Canine Renal Transplantation Model," Transplantation, 57:1717–1722 (1994).

Ogawa et al., "Effects of Leflunomide on glomerulonephritis induced by antibasement membrane antibody in rats," Agents Actions, 31:321–328 (1990).

Ogawa et al., "Therapeutic Effects of Leflunomide, a New Antirheumatic Drug, on Glomerulonephritis Induced by the Antibasement Membrane Antibody in Rats, " Clinical Immunology Immunopathology, 61:103–118 (1991).

Ono et al., "Improved technique of heart transplantation in rats," J. Thoracic Cardiovascular Surgery, 57:225–229 (1969).

Popovic et al., "Disease modifying activity of HWA 486 on the development of SLE in MRL/1–mice," Agents Actions, 19:313–314 (1986).

Schorlemmer et al., "Prolongation of Allogenic Transplanted Skin Grafts and Induction of Tolerance by Leflunomide, a New Immunosuppressive Isoxazol Derivative," Transplantation Proceedings, 25:763–767 (1993).

Schwartz et al., "Drug–induced Immunological Tolerance," Nature, 183:1682–1683 (1959).

Stecher et al., "Disease Modifying Anti–Pheumatic Drugs," Ann. Report Med. Chem. 18:171–179 (1983).

Stockman et al., "Differential Effects of cyclophosphamide on the B and T Cell Compartments of Adult Mice," J. Immunology, 110:227–282 (1973).

Thoenes et al., "Leflunomide (HWA 486) Inhibits Experimental Autoimmune Tubulointerstitial Nephritis in Rats," Int. J. Immunopharmacology, 11:921–929 (1989).

Tilney et al., "Chronic Rejection—An Undefined Conundrum", Transplantation, 52:389–398 (1991).

Turk et al., "Further Studies on B–Lymphocyte Suppression in Delayed Hypersensitivity, Indicating a Possible Mechanism for Jones–Mote Hpersensitivity," 24:751–758 (1973).

Williams et al., "Leflunomide Based Immunosuppression in Rat Cardiac and Renal Xenotransplantation," Presented at Annual Meeting of the Am. Soc. Transplant Surgeons, May 20, 1994, Chicago, IL.

Williams et al., "Leflunomide and Cyclosporic in Rat Cardiac Transplantation", Presented at Annual Meeting of the Am. Soc. Transplant Surgeons, May 1992, Chicago, IL.

Williams et al., "Leflunomide in Experimental Transplantation," Transplantation, 57:1223–1231 (1994).

Xiao et al., "Effect of Leflunomide in Control of Acute Rejection in Hamster–to–Rat Cardiac Xenografts," Transplantation Proceedings, 26:1263–1265 (1994).

Bouwan et al., "Experimental Xenotransplantation in Rodents—I: Skin Versus Heart Grafts," in Xenotransplantation, Cooper et al., eds, Springer–Verlag, Berlin (1991), pp. 323–329.

Cooper et al., "Introduction," in Xenotransplantation, Cooper et al., eds. Springer–Verlag, Berlin (191), pp. 1–7.

Steinbruchel et al., "Experimental Xenotransplantation in Rodents—Total Lymphoid Irradiation, Cyclosporine, and Monoclonal Antibodies," Xenotransplantation, Cooper et al., eds. Springer–Verlag, Berlin (1991), pp. 331–338.

Thomas et al., "Immunobiology of Xenografting in Rodents," in Xenotransplantation, Cooper et al., eds. Springer–Verlag, Berlin (1991), pp. 139–160.

Van Den Bogaerde et al., "Immunosuppression in Xenotransplantation," in Xenotransplantation, Cooper et al, eds, Springer–Verlag, Berlin (1991), pp. 161–178.

Williams et al., "Leflunomide, A Potent Immunosuppressive Molecule," International Conference on New Trends in Clinical and Experimental Immunosuppression, Geneva, Switzerland (Feb. 10, 1994).

London et al., "Islet Purification," Pancreatic Islet Cell Transplantation, Camillio Ricordi, ed; RG Landis Co., Austin, TX, pp. 113–123 (1992).

Kerckhaert et al., "Effects of Variation in Time and Dose of Cyclophosphamide Injection on Delayed Hypersensitivity and Antibody Formation," Cellular Immunology, 29:232–237 (1977).

Ricordi et al., "Islet Isolation Assessment," Pancreatic Islet Cell Transplantation, Camillio Ricordi, ed. RG Landis Co., Austin, TX pp. 132–142 (1992).

Farney et al., "Islet Autotransplantation: The Minnesota Experience," Pancreatic Islet Cell Transplantation, C. Richardi, ed., R.G. Landis Co., Austin, TX (1992), pp. 291–312.

Williams et al., "Immunosuppressive Effects of Leflunomide in a Cardiac Allograft Model," Transplantation Proceedings, 25:745–746 (1993).

PHARMACEUTICALS FOR THE TREATMENT OF REJECTION REACTIONS IN ORGAN TRANSPLANTATIONS

This is a division of application Ser. No. 07/932,577, filed Aug. 20, 1992 now U.S. Pat. No. 5,728,721.

European Patent 13,376 discloses N-(4-trifluoromethyl)-5-methylisoxazole-4-carboxanilide (compound 1) as being anti-inflammatory. Processes for the preparation of this compound are also described therein.

It is additionally known that the compound 1 and its metabolite N-(4-trifluoromethylphenyl)-2-cyano-3-hydroxycrotonamide (compound 2) have immunomodulating properties, so that they are suitable as pharmaceuticals against chronic graft versus host diseases and against autoimmune disorders, in particular systemic Lupus erythematosus (EP-A-217,206).

U.S. Pat. No. 4,061,767 describes the use of 2-hydroxyethyl-idenecyanoacetanilide derivatives for the preparation of pharmaceuticals having anti-inflammatory and analgesic action.

In the USA, 15,000 organ transplantations were performed in 1990. The majority of the transplantations relate to the kidney, but hearts, skin, lungs, liver and pancreas are also being increasingly transplanted. In a large number of the patients, which have been transplanted with an organ of another individual a reaction can occure which lead to the rejection of the grafted organ. A differentiation can be made between three forms of graft rejection:

hyperacute, acute and chronic rejection.

Hyperacute rejection is essentially caused by circulating antibodies in the blood, which are directed against the tissue of the transplanted organ (transplant), and in a very short time—often in minutes—lead to necroses of the transplant.

In acute graft rejection reaction is somewhat delayed. Further, the chronic form of graft rejection can lead to a diseasestate. In this case the transplants survive the first year after transplantation, but can be rejected in the course of the next few years. It is additional known that transplant-host relationship is not restricted to rejection by the host organism alone; in certain cases an immune reaction originating from the transplant and directed against the host tissue can occur (EP-A-217,206). A differentiation is therefore made between a rejection between transplant and host and between host and transplant.

It is additionally known that transplanted organs from different animal species for example from the mouse to the rat are also rejected (Roitt et al., Immunology, Gower Medical Publishing Ltd., 1985).

To date, no pharmaceuticals are known which offer effective protection against hyperacute rejection reaction. In the clinic, until now donors and recipients of organs have been tested for incompatibility. In 20 to 40% of all patients waiting for a transplant, do not quality for a donor organ. The acute rejection reaction can be treated, but the meditation show side effects such as nephrotoxicity during treatment. To date, there are also no medicaments known which can treat the cause of the chronic graft rejection.

The essential pathogenic factor for tissue death in the transplant is regarded to be allophilic and xenophilic antibodies (Auchincloss B., Transplantation 46, 1, 1988).

These antibodies are essentially responsible for rejection in organ transplants within an animal species (allo) or between two different species (xeno).

Surprisingly, compound 1 and its metabolite, the abovementioned compound 2, show a potent inhibition of the formation of allophilic or xenophilic antibodies. There is thus possibility effectively treating the hyperacute, acute and chronic rejection reaction of the recipient to the transplanted organ.

The invention therefore relates to the use of N-(4-trifluoromethylphenyl)-5-methylisoxazole-4-carboxanilide and N-(4-trifluoromethylphenyl)-2-cyano-3-hydroxycrotonamide and/or their physiologically tolerable salts for the preparation of pharmaceuticals for the treatment of graft rejection reactions of the organ recipient to the transplanted organ.

Suitable physiologically tolerable salts of compound 2 are, for example, alkali metal, alkaline earth metal or ammonium salts, including those of physiologically tolerable organic ammonium bases. The term organ is understood as meaning all organs in mammals, in particular the human, for example kidney, heart, skin, liver, pancreas, muscle, bone, intestine or stomach, but also blood or hair.

Rejection reaction means all defence mechanisms of the recipient organism which, in the end, lead to cell or tissue death of the transplanted organ or affect the viability of the transplanted organ.

The compounds 1 and 2 can be prepared by the following process:

A compound of the formula I

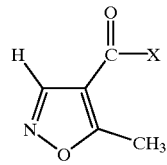

in which X represents a halogen atom, preferably chlorine or bromine, is reacted with the amine of the formula II

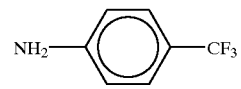

to give the compound 1, and this can then be reacted in the presence of a basic agent to give the compound 2.

The abovementioned reactions are carried out under standard conditions in a known manner (EP-B-13,376, U.S. Pat. No. 4,061,767).

The starting substances for the reactions are known or can be easily prepared by methods known from the literature.

The invention also relates to pharmaceuticals which contain an effective amount of compound 1 or compound 2 and/or physiologically tolerable salts of compound 2, in addition to pharmaceutically suitable and physiologically tolerable excipients, diluents and/or other active substances and auxiliaries.

The invention also relates to a process for the preparation of a pharmaceutical for the treatment of rejection reactions of the organ recipient against the transplanted organ, which comprises bringing compound 1 or 2 and/or a physiologically tolerable salt of compound 2 into a suitable administration form using a pharmaceutically suitable and physiologically acceptable excipient and, if appropriate, other suitable active substances, additives or auxiliaries.

The pharmaceutical according to the invention can be administered orally, topically, rectally, intravenously or alternatively parenterally. Administration is carried out before, during and after organ transplantation in the recipient and/or donor.

Suitable solid or liquid pharmaceutical administration forms are, for example, granules, powders, coated tablets, tablets, (micro)capsules, suppositories, syrups, juices, suspensions, emulsions, drops or injectable solutions and preparations having a protracted release of active substance, in whose preparation customary auxiliaries such as excipients, disintegrants, binders, coating agents, swelling agents, lubricants, flavorings, sweeteners or solubilizers are used. Commonly used auxiliaries which may be mentioned are, for example, magnesium carbonate, titanium dioxide, lactose, mannitol and other sugars, talc, milk protein, gelatin, starch, cellulose and its derivatives, animal and vegetable oils, polyethylene glycols and solvents, such as, for example, sterile water and mono-or polyhydric alcohols, for example glycerol.

Preferably, the pharmaceutical preparations are prepared and administered in dosage units, each unit containing as the active constituent a certain dose of compound 1 or 2 and/or physiologically tolerable salts of compound 2. In the case of solid dosage units, such as tablets, capsules or suppositories, this dose can be up to about 300 mg, but preferably 10 to 200 mg.

For the treatment of a patient (70 kg) to whom an organ has been transplanted, in the early phases after transplantation an intravenous infusion treatment of at most 1200 mg per day and in the later rehabilitation phases an oral administration of 3 times 300 mg per day of compound 1 or 2 and/or of the corresponding salts of compound 2 are indicated.

Under certain circumstances, however, higher or lower doses may also be appropriate. The administration of the dose can be carried out both by single administration in the form of an individual dosage unit or else several smaller dosage units and by multiple administration of subdivided doses at specific intervals.

Finally, compound 1 or 2 and/or its corresponding salts can also be combined during the preparation of the above-mentioned pharmaceutical administration forms together with other suitable active substances, for example antiuricopathics, thrombocyte aggregation inhibitors, analgesics and steroidal or non-steroidal anti-inflammatories.

EXAMPLE 1

Pharmacological Tests and Results 2 to 3 month-old rats (LEW) are intraperitoneally (i.p.) sensitized with $2 \times 10^7$ human peripheral blood lymphocytes The i.p. administration of compound 2 starts 4 days before sensitization and ends 10 days after sensitization of the rats. Serum samples are taken from the tail vein and stored at −80° C.; the activity of complement is avoided by heat deactivation.

The naturally occurring xenophilic antibodies (NXA) and the xenophilic antibodies induced by sensitization (SXA) are titrated and live human peripheral blood lymphocytes are added (45 min. at 20° C.). After intensive washing, FITC-labeled goat-anti-rat IgG or IgM antibodies are added and the binding to SXA or NXA is quantitatively determined by flow cytometry (FACScan, Becton Dickinson).

A) Non-sensitized Rats

The serum of male LEW rats contain NXA which bind to vital human peripheral blood lymphocytes, to be precise, usually with an average IgM titer of 1:4 and an average IgG titer of less than 1:1. The rats (n=8) which are treated every day with 10 mg/kg of compound 2, show a 30% reduction in their IgG titer and a 50% reduction in their IgM titer on the 11th day.

B) Sensitized Rats

In sensitized rats there are greatly increased amounts of SXA The IgG titer is 1:1024 to 1:16384 and the IgM titer 1:4 to 1:256. The IgG titer remains stable for over 50 days, while the IgM titer slowly decreases after the 10th day.

The sensitized rats (n=5) are treated with 3 or 10 mg/kg of compound 2. The following SXA titers are tound on the 11th day:

| Compound (mg/kg) | IgG | IgM |
|---|---|---|
| 0 | 1:2048 | 1:90 |
| 3 | 1:25 | 1:16 |
| 10 | 1:1 | 1:1.5 |

The action of compound 2 on the formation of allophilic antibodies.

Male Brown-Norway rats with a weight of 200 to 250 g are used as heart donors. The hearts are transplanted into male Lewis rats of the same weight. All rats are supplied with a standard diet and water and kept in an environment with 12 hours of light and darkness.

On the day of heart transplantation and then at intervals of 4 days, 1 ml of blood in each case is taken from the tail vein of the recipient rats (Lewis rats). The titer of allophilic antibodies in the blood of the recipient rats is determined by incubating various dilutions of the recipient blood with spleen cells of the donor rats (Brown-Norway rats) and rabbit complement. The cytotoxicity is determined by the Trypan Blue exclusion method. The p value for the antibodies is determined using the standard t-test and compared with the untreated control animals.

Treatment with compound 2 begins on the 4th day after transplantation. 10 mg/kg of compound 2 in each case are administered i.p. once per day. The number of animals which are simultaneously treated is 5 (n=5). Treatment ends on the 17th day. The following table shows the mean of the cytotoxicity values (%) during the treatment.

| serum Dilution | Days after transplantation | | | | | | p value on the 17th day |
|---|---|---|---|---|---|---|---|
| | 0 | 4 | 7 | 11 | 14 | 17 | |
| 1:5 | 3 | 63 | 36 | 19 | 22 | 11 | 0.001 |
| 1:25 | 3 | 58 | 31 | 16 | 11 | 6 | 0.001 |
| 1:125 | 4 | 34 | 20 | 9 | 6 | 5 | 0.050 |

EXAMPLE 2

Preparation of N-(4-trifluoromethyl)-5-methylisoxazole-4-carboxanilide (Compound 1)

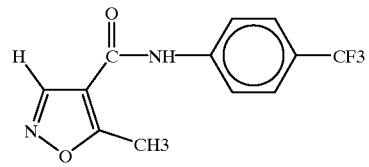

A solution of 0.05 mol of 5-methylisoxazole-4-carbonyl chloride (7.3 g) in 20 ml of acetonitrile is added dropwise at room temperature to a solution of 0.1 mol of 4-trifluoromethylaniline (16.1 g) in 150 ml of acetonitrile. After stirring for 20 minutes, the precipitated 4-trifluoromethylaniline hydrochloride is filtered off with suction and washed twice with 20 ml of acetonitrile each time, and the combined filtrates are concentrated under reduced pressure. 12.8 g of white, crystalline N-(4-trifluoromethyl)-5-methylisoxazole-4-carboxanilide (compound 1) are thus obtained.

EXAMPLE 3

Preparation of N-(4-trifluoromethylphenyl)-2-cyano-3-hydroxycrotonamide (compound 2)

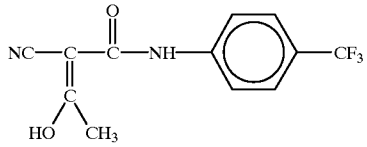

0.1 mol of N-(4-trifluoromethyl)-5-methylisoxazole-4-carboxanilide is dissolved in 100 ml of methanol and treated at +10° C. with a solution of 0.11 mol (4.4 g) of sodium hydroxide in 100 ml of water. The mixture is stirred for 30 minutes and, after diluting with water, is acidified with concentrated hydrochloric acid. The precipitated crop of crystals is filtered off with suction, washed with water and dried in air. The yield is 24.4 g of N-(4-trifluoromethylphenyl)-2-cyano-3-hydroxycrotonamide (compound 2). Melting point from methanol 205 to 206° C.

EXAMPLE 4

Acute Toxicity After Intraperitoneal Administration

The acute toxicity after intraperitoneal administration of the test substances was determined with NMRI mice (20 to 25 g) and SD rats (120 to 195 g). The test substance was suspended in a 1% strength sodium carboxymethyl-cellulose solution. The different dosages of the test substance were administered to the mice in a volume of 10 ml/kg of body weight and to the rats in a volume of 5 ml/kg of body weight. Per dosage, 10 animals were used. After 3 weeks, the acute toxicity was determined by the method of Litchfield and Wilcoxon. The results are summarized in the table.

TABLE

|  | Compound 1 acute toxicity intraperitoneal $LD_{50}$ (mg/kg) | Compound 2 acute toxicity intraperitoneal $LD_{50}$ (mg/kg) |
| --- | --- | --- |
| NMRI mouse | 185 (163–210) | 150 (100–200) |
| SD rat | 170 (153–189) |  |

What is claimed is:

1. A method of treating chronic allograft rejection reaction of an organ recipient to a transplanted organ, which comprises administering to said organ recipient an effective amount of at least one compound having the formula I or II:

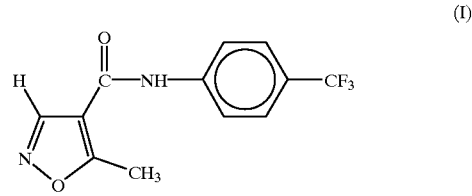

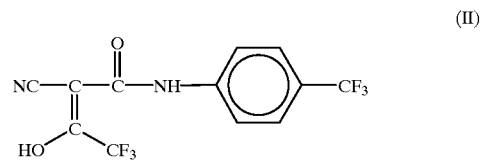

wherein the compound of formula II can also be administered in the form of a physiologically tolerable salt.

2. The method as claimed in claim 1, wherein the compound of formula I is administered to the organ recipient.

3. The method as claimed in claim 1, wherein the compound of formula II is administered to the organ recipient.

4. The method as claimed in claim 1, wherein at least one compound of formula I and formula II is administered in dosage units in an amount up to about 300 mg.

5. The method as claimed in claim 4, wherein the amount in a dosage unit ranges from about 10 mg to about 200 mg.

6. The method as claimed in claim 1, wherein said at least one compound of formula I and formula II is administered in an amount up to about 900 mg per day per 70 kg of body weight.

7. The method as claimed in claim 6, wherein the amount administered is given in dosage units of up to about 300 mg, three times a day.

8. The method as claimed in claim 1, wherein said at least one compound of formula I and formula II is combined with at least one pharmaceutically active ingredient suitable for administration.

9. The method as claimed in claim 8, wherein said at least one pharmaceutically active ingredient is chosen from an antiuricopathic, a thrombocyte aggregation inhibitor, an analgesic, and an anti-inflammatory agent.

* * * * *